United States Patent [19]

Pawliszyn

[11] Patent Number: 4,993,832

[45] Date of Patent: Feb. 19, 1991

[54] METHOD AND APPARATUS FOR DETECTING CONCENTRATION GRADIENTS

[75] Inventor: Janusz B. Pawliszyn, Waterloo, Canada

[73] Assignee: Anthony R. Torres, Salt Lake City, Utah

[21] Appl. No.: 271,008

[22] Filed: Nov. 14, 1988

[51] Int. Cl.⁵ .......................................... G01N 21/41
[52] U.S. Cl. ..................... 356/128; 356/129
[58] Field of Search ............................. 356/128–132, 356/344, 432, 362

[56] References Cited

U.S. PATENT DOCUMENTS

| | | | |
|---|---|---|---|
| 2,780,955 | 2/1957 | Wiedemann | 356/128 |
| 3,623,361 | 11/1971 | Funk, Jr. | 356/129 |
| 4,547,071 | 10/1985 | Teitelbaum | 356/129 |
| 4,673,810 | 6/1987 | Babsch et al. | 250/231 |
| 4,784,494 | 11/1988 | Pawliszyn | 356/128 |

OTHER PUBLICATIONS

Dual Beam Laser Deflection Sensor; Review of Scientific Instruments; Sep. 1985, vol. 56, No. 9, Janus Pawliszyn, Michael Weber, Michael Dignam.

Primary Examiner—Richard A. Rosenberger
Assistant Examiner—Hoa Pham
Attorney, Agent, or Firm—Mallinckrodt & Mallinckrodt

[57] ABSTRACT

A differential, sequential detector, and method, for detecting refractive index gradients in a sample and for producing an output signal approximating a derivative of the refractive index gradient utilizes two closely spaced, parallel probe light beams passing through the sample with the beams separated along the direction of any expected gradient to be detected. A sensor is arranged to measure and produce an output signal proportional to the difference in movement of the two beams. The sensor is preferably arranged so that only complementing portions of each beam will fall on the sensing area of the sensor so that parallel movement of the beams will change equally the respective complementary portions sensed to maintain a constant output from the sensor, but movement of one beam relative to the other beam will produce a change in the sensor output proportional to the relative movement and approximating the derivative of refractive index gradient causing the relative beam movement. Rather than using two, closely spaced beams, a similar output can be obtained using a wide, single beam.

19 Claims, 7 Drawing Sheets

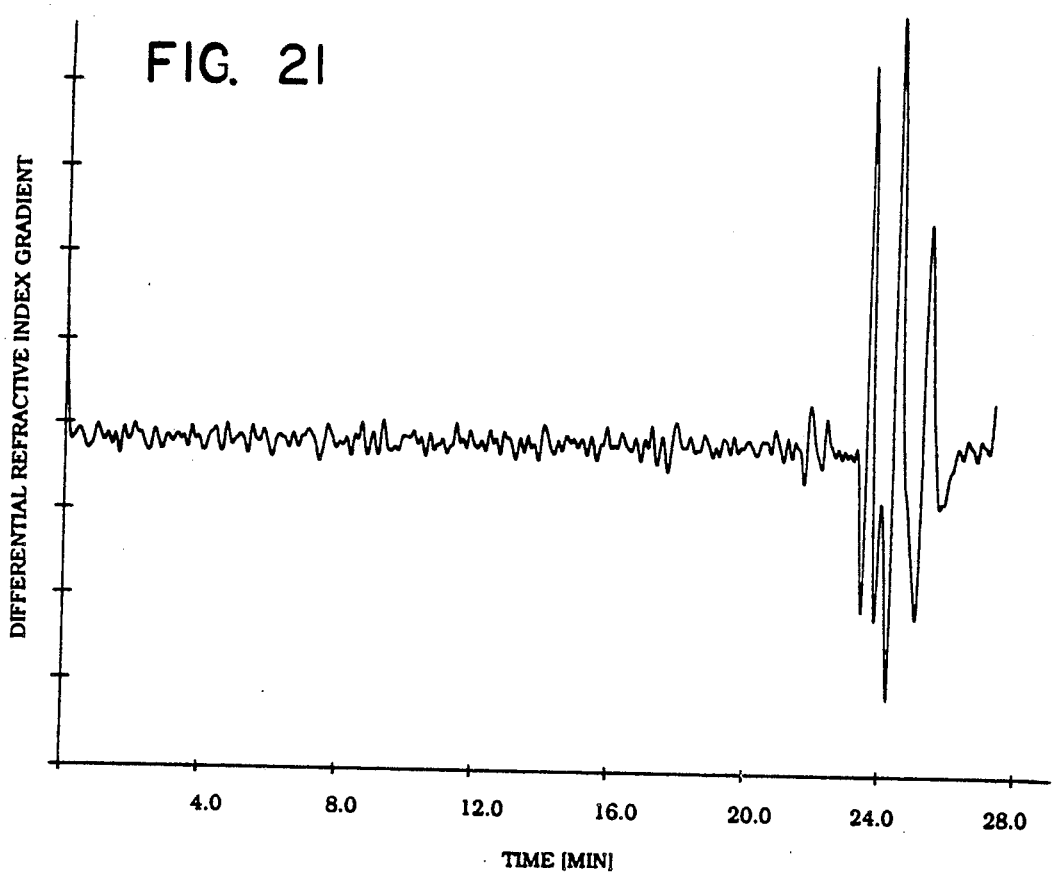
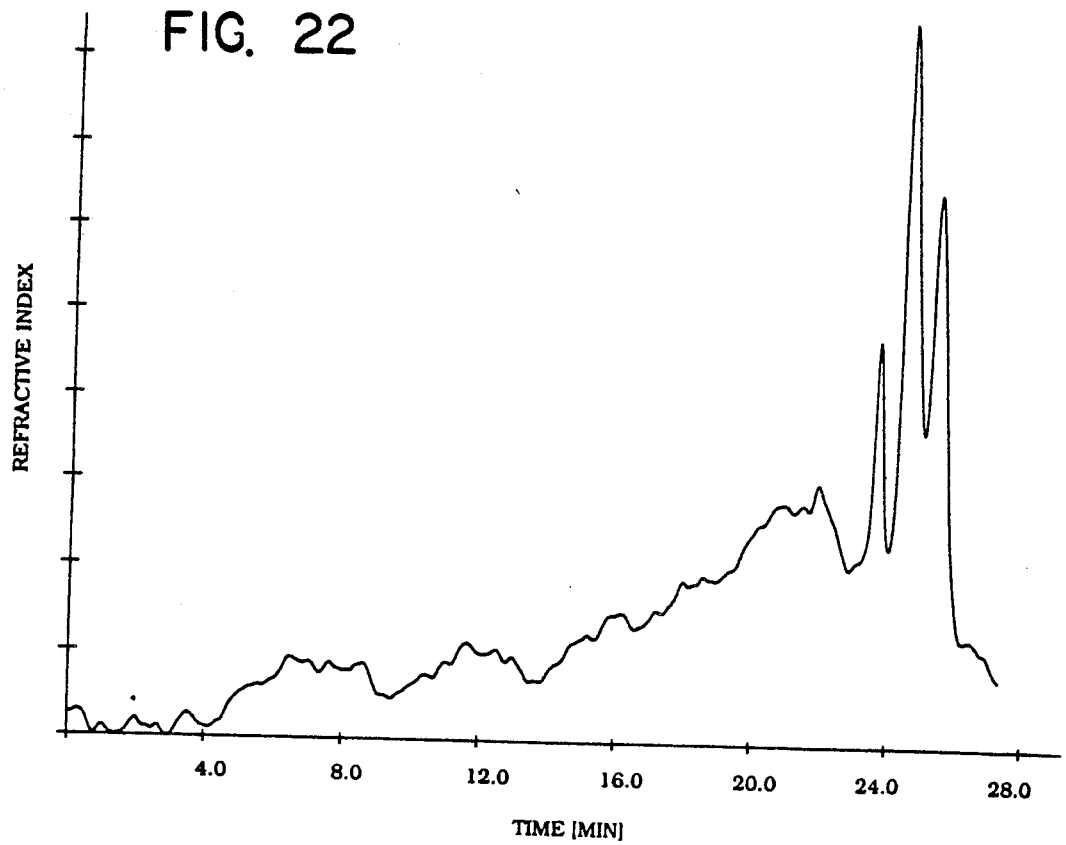

METHOD AND APPARATUS FOR DETECTING CONCENTRATION GRADIENTS

BACKGROUND OF THE INVENTION

1. Field:

The invention is in the field of detection methods and apparatus based on Schlieren optics.

2. State of the Art:

It has been known for some time that a refractive index gradient such as produced by a concentration gradient in a fluid such as a gas, liquid or supercritical fluid, will cause deflection of light passing through the gradient. The optical method of observing and measuring the deflection of light caused by refractive index gradient fields is generally referred to as Schlieren optics. In the past, Schlieren images resulting from light deflections have been recorded on photographic plates and the plates then analyzed for light intensity distribution using densitometers. Recently, evaluation of the photographic images has been done by computer. These methods are useful in studying plasmas where very complicated toroidal and parabolic shapes are generated.

U.S. Pat. No. 4,547,071 discloses a sensor for measuring density gradients in a nonhomogenious fluid sample using Schlieren optics. In such sensor, a laser light beam is directed through a sample chamber and is moved along said chamber. A quadrant light position sensor located on the opposite side of the chamber detects the deflection of the laser light beam as it is moved through the sample. The amount of deflection indicates the density gradient at any point in the sample. Rather than moving the laser beam along the sample chamber, the beam can be held constant and the sample moved within the chamber.

A current development in the field of high performance liquid chromatography is the open tubular capillary column which provides ultra high efficiency separation of sample components. This method can utilize very small sample volumes. Similarly, current capillary zone electrophoresis equipment can be used with extremely small volume samples. In my copending application Ser. No. 948,217 filed Dec. 31, 1986, now U.S. Pat. No. 4,784,494, I show a detector that can be used to detect concentration and thermal gradients in very small samples. That detector utilizes a light source to generate a probe beam of light that is passed through the sample having the gradient to be detected or measured and the deflection of the probe beam is measured on a beam position detector. Various light sources may be used to generate the probe beam such as a laser or light emitting diode (LED). The LED source has been found to be much more positionally stable over time than a laser light source so the LED source is preferred where it can be used. However, where very small samples are used with very small sample chambers, such as sample chambers made of capillary tubes with inside diameters through which the samples flow of as small as 10 micrometers, the probe light beam used has to be very sharply focused inside such chambers. Since laser light beams are more easily focused than the LED beams, lasers currently are the only practical light source for use with such very small sample chambers. As indicated, laser light beams are not very positionally stable and tend to drift over time which complicates using a measuring system as shown in my referenced application which measures position of the probe beam as an indication of gradients in the sample. Positional drift of the probe light beam will create inaccuracies in the measurements.

Current work, other than that indicated in my referenced patent application, has focused on concentration measurement and uses various differential arrangements to try to correct for temperature fluctuations and gradient elution conditions that are known to restrict the performance of such detectors. However, problems remain and the need for an accurate detector for very small volume samples in very small volume sample chambers remain.

Detectors which utilize parallel probe beams have been tried as disclosed in my co-authored paper entitled "Dual-Beam Laser Deflection Sensor" published in the September 1985 issue, Vol. 56, No. 9, of *Review of Scientific Instruments*, pages 1740–1743. The attempt there was to provide a sample probe beam and a parallel control beam that did not pass through the gradient and to measure the differential movement of the beams to compensate for the positional instability of the laser light source. The positional change of each laser beam was measured using a position detector for each beam which had two outputs which varied with movement of the beam in one dimension of movement. For convenience, the detectors for each beam took the form of one half of a single quadrant detector. While the detector described in the article showed improvement over other detectors, the improvement was not as great as expected.

Another problem with detectors, particularly the detectors measuring concentration directly, and to a lesser extent detectors measuring the concentration gradient, is the presence of low frequency noise in the output. This low frequency noise is caused by drift and broad peaks due to temperature fluctuations and compositional variations of the medium in which the separated materials to be detected are carried. While reduction of high frequency noise when the signal is of low frequency can be accomplished by using low pass filters in analog or time domain, it is a more challenging task to reduce the low frequency noise such as caused by drift and broad peaks. The main reason for difficulty in reducing low frequency noise is that the desired sharp peaks produced by material to be detected also contain low frequency information. In other words, it is impossible to filter out drifts without changing the shape of a Gaussiam peak. The frequency range which differentiates peaks from drifts are mid-range frequencies. Broad drifts do not contain information in this region while sharp peaks extend to these frequencies. Therefore, any filter which emphasizes mid-range will be able to eliminate drifts successfully. As it has been noted above, any change in low frequencies will result in a different signal shape. It is important, therefore, to apply a filter which will produce a well defined signal shape with magnitude directly related to the concentration of the sample being detected.

It is well known that differentiation or derivitization can reduce drifts substantially. Differentiation in the time domain corresponds to the application of a low pass filter in the frequency domain:

$$\frac{d^n f(t)}{dt^n} = (iw)^n F(w)$$

where n is an order of the derivative, F(w) is a time output f(t) described in the frequency domain, and w is frequency. For example, the first derivative of the concentration signal in the time domain is equivalent to a linear filter in the frequency domain. Higher order derivatives, such as second order derivatives are even better able to filter low frequency noise.

During derivitization, the Gaussian peak of a given height $C_{max}$ is converted into a derivative of magnitude:

$$\left(\frac{dC}{dx}\right)_{max} = \frac{e^{-\frac{1}{2}}}{\sigma} C_{max}$$

where $\sigma$ is the standard deviation of the chromatographic peak in units of length. This relationship strongly indicates that the magnitude of the gradient at the inflection points of the Gaussian peak increases faster than its height when the peak narrows. In other words, relative sensitivity enhancement of the gradient measurement increases with improvement in the efficiency of the separation process. This effect is more pronounced if a second derivative response detector is used:

$$\left(\frac{d^2C}{dx^2}\right)_{max} = \frac{1}{\sigma^2} C_{max}$$

Also, the second derivative of the signal resembles a peak much sharper than the original Gaussian which can result in a higher resolution of the chromatogram.

The simplest way to generate a derivative response is to apply mathematical differentiation to a lower order signal output. However, this approach is not very useful in practice since higher frequency noise is multiplied simultaneously by this process. The best results would be achieved by a detector which directly produces a derivative or a differential response.

SUMMARY OF THE INVENTION

According to the invention, a detector for detecting refractive index gradients within a sample along a gradient direction and providing an output signal approximately proportional to a derivative of the refractive index gradient detected, includes a sensor having a sensing surface extending along the direction of the expected gradient to be detected for a distance less than the length of the expected gradient in the gradient direction. Light, from a source of light, is directed through the sample so that a portion of the light passing through the sample falls on the sensing surface of the sensor, a portion of the light falls off the sensing surface of the sensor on one side of the sensing surface along the gradient direction and a portion of the light falls off of the sensing surface of the sensor on the opposite side of the sensing surface along the gradient direction. The portions of light falling off the opposite sides of the sensing surface are complementary portions so that movement of the light not caused by presence of a refractive index gradient in the path of the light, such as movement caused by vibration or positional instability of the light source, will move equally in the same direction the respective complementary portions of the light so that any increase in light falling off of the sensing surface at one side is equal to the increase in light falling onto the sensing surface at the other side to thereby maintain a constant output from the sensor. Movement of the complementing portions of the light with respect to one another as caused by a refractive index gradient in the path of the light will produce either an increase or a decrease in the intensity of the light falling on the sensing surface and will produce an output of the sensor proportional to the relative movement of the light and approximating a derivative of the refractive index gradient causing the movement of the light.

The light passing through the sample and falling partially on and partially off the sensing surface of the sensor may be a pair of closely spaced light beams separated in the gradient direction or may be a single light beam. Further, the sample in which the gradient is to be detected may be in a sample chamber through which the sample containing the expected gradients flow, or may be a gradient created above a surface, such as an electrode surface or a membrane surface as by electrochemical processes or mass flow processes, or may be gradients formed by chemical reactions.

A preferred differential, sequential detector which measures a refractive index gradient in a sample utilizes two closely spaced, parallel probe light beams passing through the sample with the beams separated along the direction of any expected gradient to be detected and a sensor to sense and measure differential movement of the two beams. The two probe beams are preferably generated by the same light source, such as the same laser, and then split into parallel separate beams. When the beams are passing through a sample without a gradient present, the sensor senses only complementing portions of each beam so that if the beams move in parallel, as would be the case during beam positional shifts of a source laser, the output of the sensor remains the same. If relative movement occurs between the two beams as will occur as a different refractive index gradient is encountered by each beam, an output is produced by the sensor proportional to the relative beam movement.

The sensor preferably includes a single photodiode initially calibrated so that one half of each of the beams fall on the photodiode at a sharp edge of the sensing surface. This can be accomplished by providing a mask over the photodiode to provide a sharp edge for the sensing surface and positioned so that the probe beams are divided in half with the halves toward each other falling on the sensing surface. The division of the beams will be along lines transverse to the direction of any expected gradient to be measured. In this way, when one beam moves in the gradient direction with respect to the other beam, i.e., the beams move toward one another or away from one another, either more of the beams or less of beams fall on the sensing surface so the output of the sensor is either increased or decreased, respectively. However, any parallel movement of the probe beams in the gradient direction will cause less one beam to fall on the sensing surface but an equal amount more of the other beam to fall on the surface so that the overall light falling on the surface is the same. When the parallel probe beams are created by splitting a single laser beam into two beams, the positional instability of the laser will create parallel movements of the parallel beams. Since parallel movements of the probe beams are cancelled out by the sensor, the sensor output has been compensated for the laser positional instability.

Since the detector uses either two closely spaced parallel beams or a single beam which is wide enough to simulate the two closely spaced parallel beams, and measure the difference in movement of the two beams or the light within the single beam, the output of the sensor of the detector automatically provides a signal approximately proportional to the derivative of the refractive index gradient and therefore approximately proportional to the second derivative of the concentration itself. Therefore, the detector significantly reduces the amount of low frequency noise in the output signal to provide a much cleaner and sharper indication of sample constituents.

THE DRAWINGS

The best mode presently contemplated for carrying out the invention is shown in the accompanying drawings in which:

FIG. 1 is a schematic representation of a light beam passing through a gradient;

FIG. 2, a schematic representation of a light beam passing through a sample chamber, showing the deflection angle produced by the presence of a refractive index gradient in the chamber;

FIG. 3, a second schematic representation of a light beam passing through a sample chamber with a concentration gradient;

FIG. 4, a schematic representation similar to that of FIG. 3, but showing an additional, parallel probe light beam passing through the sample chamber;

FIG. 5, a comparision of a curve representing the concentration profile of a sample sent through a detector of the invention with curves representing the movement of the individual probe beams of the detector and a curve produced as the output signal by the detector;

FIG. 6, a schematic representation of a detector of the invention;

FIG. 7, a front view of the light beam sensor of FIG. 6;

FIG. 8, a vertical section through the sensor of FIG. 7 taken on the line 8—8 of FIG. 7;

FIG. 9, a front view of the light beam sensor of FIG. 7 similar to that of FIG. 7, but showing the light beams in a different position;

FIG. 10, another similar front view of the sensor showing the light beams in a still different position;

FIG. 11, a circuit diagram of circuitry usable with the invention;

FIG. 12, a circuit diagram of a different embodiment of circuitry usable with the invention;

FIG. 13, a fragmentary schematic representation of the detector of FIG. 6, showing a modification to a portion thereof;

FIG. 14, a circuit diagram similar to that of FIG. 12, but showing two reference photodiodes;

FIG. 15, a circuit diagram of still different circuitry usable with the invention;

FIG. 16, a perspective view of a different embodiment of sensor;

FIG. 17, a front view of the sensor of FIG. 16, showing a single light beam falling thereon;

FIG. 18, a comparison of a curve generated by the detector of the invention during a flow injection test representing the second derivative of the concentration of the sample injected into the sample chamber with a calculated curve indicating the first derivative and with a curve representing the concentration profile;

FIG. 19, a schematic representation of the construction of a sample chamber used in testing the invention;

FIG. 20, a schematic representation of an electrophorsis apparatus used in testing the invention;

FIG. 21, the output of the detector of the invention during an electrophoresis test using the apparatus of FIG. 20; and FIG. 22, a calculated representation of the concentration profile resulting in the output of FIG. 21.

DETAILED DESCRIPTION OF THE PREFERRED EMBODIMENT

Figure 1:
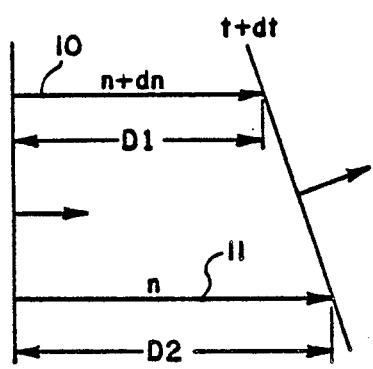

It is well known that light passing through a refractive index gradient in a solution is deflected. The physical reason for light deflection when passing through this gradient lies in the relationship between the refractive index and light propagation velocity. Different parts of the light advance to a different degree with time, which generates the phase shift. Thus, as shown in FIG. 1, during a given time period t+dt, light at the top of a light beam indicated by arrow 10 which is passing through a solution with a refractive index of n+dn will travel a distance of D1. The light at the bottom of the light beam indicated by arrow 11 which is passing through a solution with a refractive index of n will travel a distance D2. This results in a tilt of the light wavefront and since light travels perpendicular to the wavefront, the light beam is tilted as illustrated. In FIG. 1, D2 is greater than D1 resulting in an upward tilt, but depending upon the values of n and n+dn, the tilt could be downward.

The light path through the refractive index gradient can be calculated by using the Fermat principle that the light path through the medium is such that the time necessary for its traversal is minimum. The relationship between the angle of deflection, $\theta$, and the refractive index gradient normal to the light propagation dn/dx and path length through this gradient, D, can be written as $$\tan \theta = \sin h(D/n)(dn/dx) = (D/n)(dn/dx) + (dn/dx)^3(D^3/n^3 3!) + (dn/dx)^5(D^5/n^5 5!) + \ldots$$

where n is the refractive index of the medium. In situations where the sensor of the invention will be used, D and $\theta$ are small. We can then approximate:

$$\theta = (D/n)(dn/dx)$$

Figure 2:
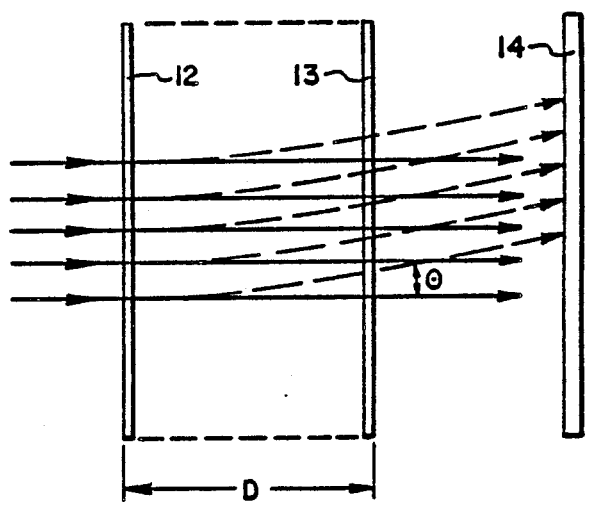

FIG. 2 illustrates the detection principle behind this method. With a nonuniform distribution of a solute in the sample chamber shown schematically between sample chamber walls 12 and 13 giving a sample chamber distance D, a concentration gradient is established. This gradient forms the corresponding refractive index gradient $dn/dx = (dn/dc)(dc/dx)$, which then tilts or deflects the propagating light beam by angle $\theta = (D/n)(dn/dc)(dc/dx)$. This deflection can be measured by measuring the position of the light beam on the position detector 14. The information produced during the measurement of the concentration gradient relates to the universal property of the solute—refractive index n. Consequently, the concentration gradient produced by any solute that has a different n than the solvent will be detected by noting a deflection or tilt in the light beam.

Figure 3:
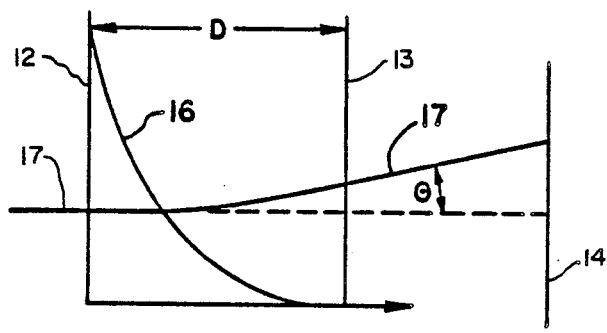

FIG. 3 shows the same principal as FIG. 2, but illustrates it somewhat differently. Thus, if a concentration gradient represented by line 16 exists in a sample in a sample chamber defined by walls 12 and 13, a probe beam of light 17 directed through the sample will be deflected as indicated above by an angle $\theta$. This causes the position of the beam to move on the surface of the position sensor 14 as indicated above.

Figure 4:
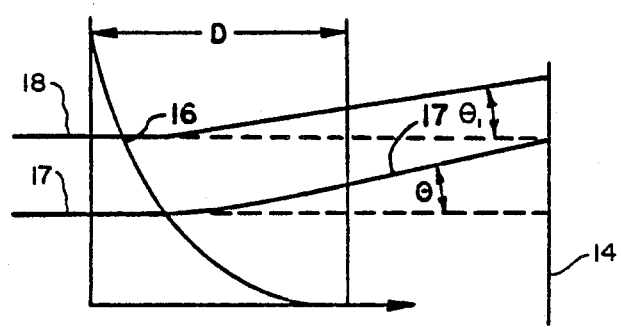

If an additional probe beam 18 is directed through the sample chamber parallel to probe beam 17 but spaced in the direction of the gradient from beam 17, see FIG. 4, each of the beams will pass through a different portion of the gradient and will therefore have different angles of deflection. Thus, beam 17 is deflected an angle $\theta$ while beam 18 is deflected an angle $\theta_1$. If the sensor 14 can measure the difference in deflection of the two beams, a measurement representing and approximating the first derivative of the concentration gradient can be obtained. Since the measurement of the concentration gradient is the first derivative of the actual concentration, the differential measurement of the concentration gradient approximates the second derivative of the concentration.

The same effect can be obtained if a single light beam of width sufficient to encompass both of the beams 17 and 18 in FIG. 4 is passed through the gradient because different parts of the single beam will be deflected differently so that a distinctive concentration pattern within the single beam on sensor 14 will be produced. Similarly, if the sensor 14 can measure the difference in deflection between different parts of the beams, e.g. the top and bottom parts of the beam, the same measurement approximating the derivative is obtained.

Figure 6:
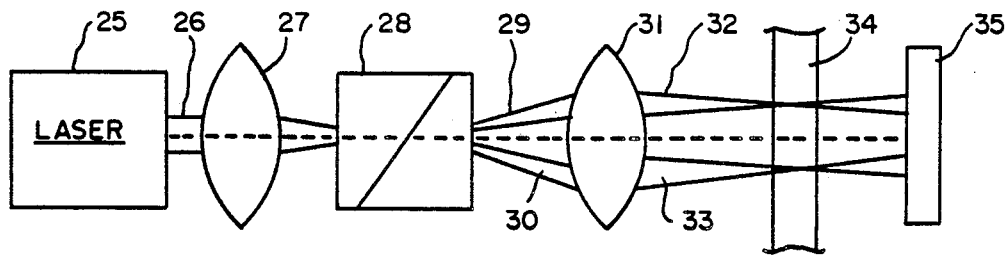

A detector of the invention is shown schematically in FIG. 6. The detection apparatus includes a laser 25, which generates a laser beam 26 directed to a lens 27 which focuses the beam into a Wollaston prism 28. The Wollaston prism 28 splits the beam 26 into two beams 29 and 30. A lens 31 is positioned in the path of the two beams 29 and 30 so as to focus the beams as two parallel beams 32 and 33 passing through a sample chamber 34. The distance between the parallel beams is adjusted by adjusting the distance between Wollaston prism 28 and lens 31. The sample chamber 34 is located at the focal point of the parallel probe beams. After passing through the sample chamber, the parallel probe beams 32 and 33 fall on a sensor 35 which measures the relative movement of one probe beam with respect to the other, i.e., measures the differences in movement of the two beams.

Figure 5:
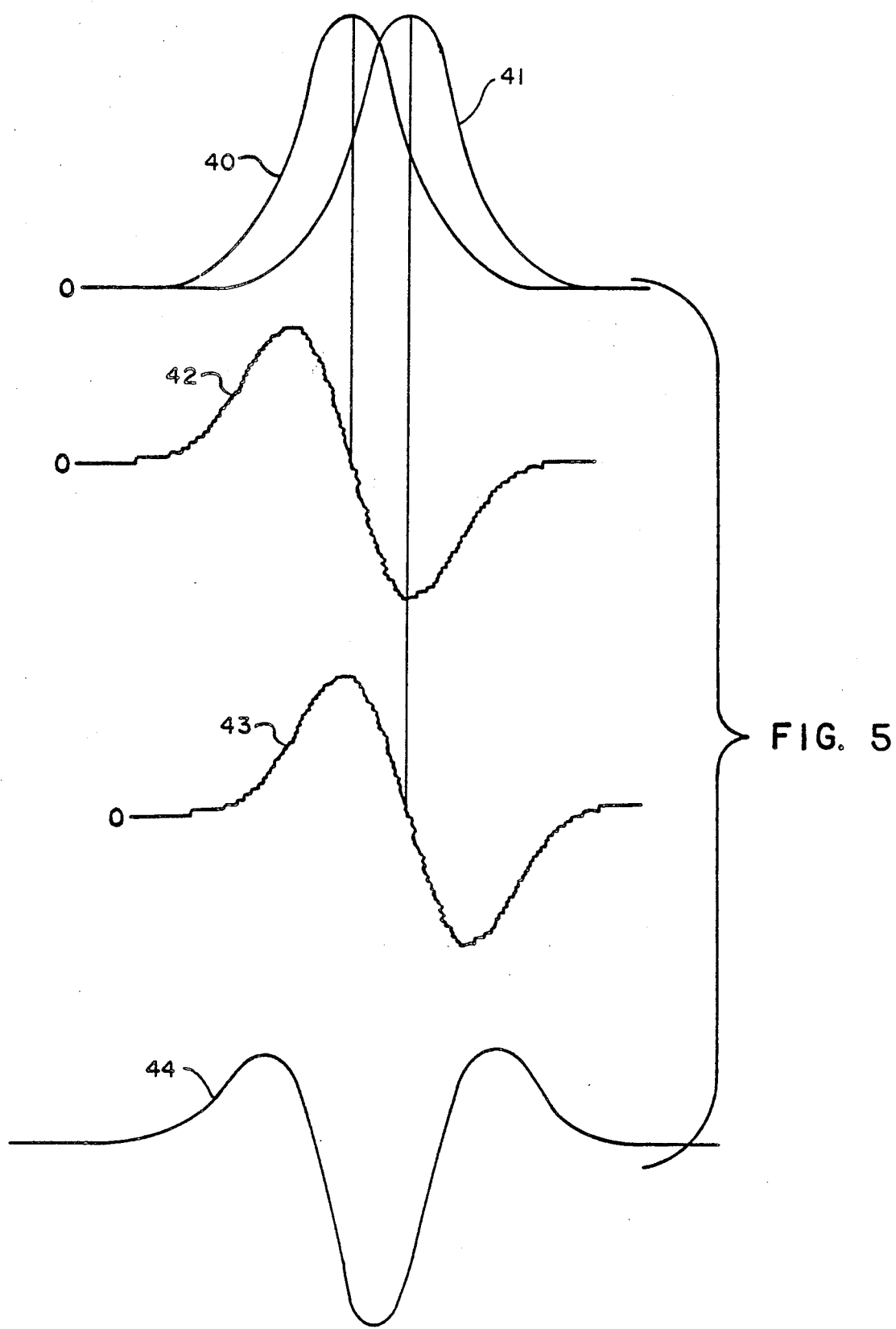

The relationship of the two beams and the resulting detector output are shown in FIG. 5. A sample flowing from a chromatography column will have a series of components spaced in time in a mobile phase. If water is used with the column as the mobile phase, the sample eluting from the column consists of a stream of water in which various separated components to be determined, as separated by the column, are spaced. Thus, concentration gradients exist in the sample as the sample stream changes from pure water to each component solution and back again. The concentration profile of a particular component in the sample stream will theoretically have a Gaussian shape as shown by curve 40 in FIG. 5. This is because some dispersion of the component in the water carrying it will occur. In practice, the concentration profile is usually close to a Gaussian shape. The O axis for curve 40 represents the carrier or solvent and the distance along the horizontal axis represents time. The concentration of a component will increase rapidly to a peak value and then decrease rapidly back to the solvent. The height of the peak will depend upon the amount of the component present. This Gaussian concentration profile of a component in a sample will remain substantially constant in the sample as it passes through the sample chamber so that each location along the length of the sample chamber will see the same concentration profile, but at a different time. Thus, if a concentration gradient 40 passes through the sample chamber 34 of the detector of FIG. 6, such concentration gradient 40 will pass through upper probe beam 32 as indicted in FIG. 5, but will pass through lower probe beam 33 at a later time as indicated by curve 41, FIG. 5, which is identical to curve 40 but is displaced to the right along the horizontal axis.

A concentration gradient is present in the sample as the concentration of a component increases and decreases. This causes each of the probe light beams to be deflected as shown in curves 42 and 43. Curves 42 and 43 are identical, but since curve 42 is generated by upper probe beam 32 in response to concentration profile 40, it is aligned with profile 40. Curve 43 is generated by lower probe beam 33 in response to the concentration profile at the delayed time it passes through beam 33, shown as curve 41, and is thus in response to and is aligned with curve 41. As to each of curves 42 and 43, as the concentration gradient shown by curves 40 and 41, respectively, passes its inflection point, the deflection of the respective probe beams reach a peak. From the inflection point, the concentration gradient decreases as the concentration itself continues to increase. Thus, the deflection of the probe beams decrease. As the concentration reaches a peak, the probe beam deflections becomes zero as shown by the zero crossover of curves 42 and 43. As the concentration drops, a concentration gradient again exists and the probe beams are deflected in the opposite direction causing the negative peaks of the curves 42 and 43 and then as the concentration change decreases and becomes only solvent again, the deflection of the probe beams 42 and 43 move back to zero deflection. It will be recognized that each of the curves 42 and 43 generated by measuring the concentration gradient is a first differential of the concentration profiles 40 and 41.

If the difference between curves 42 and 43 is measured, a curve 44 is produced which is approximately a differential of the curves 42 and 43 and approximately a second differential of the concentration profile represented by curve 40 or 41. Thus, if the sensor 35 measures and provides directly an output equivalent to curve 44, which is the difference between the individual probe beam deflections, the detector provides an output closely approximating the second derivative of the concentration.

The sensor 35 of FIG. 6 is constructed so that it measures only complementary portions of each probe beam when no refractive index gradient is present in the sample so that parallel movement of the beams, such as might result from vibrational movement of the laser or from movement of the laser beam resulting from the inherent positional instability of the laser beam, will change substantially equally the respective complementing portions of the beams sensed to maintain a constant output from the sensor, but so that movement of one beam with respect to the other beam, as when the beams are each deflected by a concentration gradient to different degrees, will provide an output of the sensor proportional to the relative movement of the beams. In the particular embodiment shown, the sensor is constructed with a single photosensor 50, FIGS. 7-10, such as a single photodiode. An S1087-01 from Hammamatsu of Middlesex, New Jersy has been found satisfactory.

Figure 7:
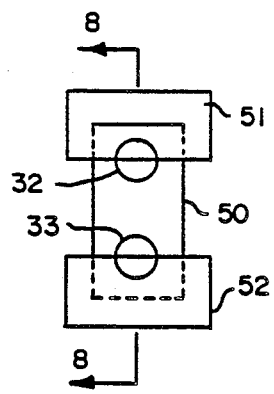
Figure 8:
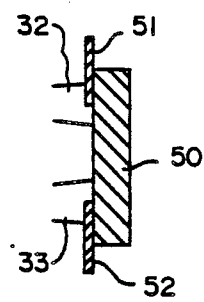
Figure 9:
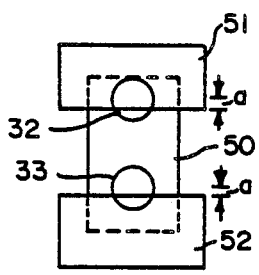

The upper and lower ends of rh photosensor 50 are covered or masked by upper and lower end covers 51 and 52, respectively, which are preferably position adjustable with respect to photosensor 50. The sensor 35 is positioned with respect to upper and lower probe light beams 32 and 33 such that for each beam, one half of the beam falls on the photosensor and one half of the beam falls on an end cover. Thus, as shown in FIGS. 7 and 8, the photosensor 50 and the end covers 51 and 52 are positioned so that with no refractive index gradient present in the sample chamber so that probe beams 32 and 33 pass directly through the chamber without being deflected, the lower half of upper beam 32 falls on photosensor 50 and the upper half of upper beam 32 falls on cover 51 and is thereby blocked from falling on photosensor 50. The upper half of lower beam 33 falls on photosensor 50 and the lower half of lower beam 33 falls on cover 52 and is blocked from photosensor 50. Thus, only one-half of each beam falls on the photodetector. With this arrangement, if the probe beams move in parallel, such as would occur due to the positional instability of a laser light source for the probe beams or would occur due to vibration of the laser, the output of the sensor remains the same and such movement and instability is compensated for. For example, if the probe beams both move upwardly a distance "a" as shown in FIG. 9, more of beam 32 falls onto cover 51 and less onto photosensor 50. However, now less of beam 33 falls onto cover 52 and more falls onto photosensor 50. The portion of beam 32 moving onto cover 51 equals the portion of beam 33 moving onto photosensor 50 so the net result due to the parallel movement of the beams is that the same amount of light falls onto the photosensor before and after the parallel movement of the beams so the sensor sees no change and no change in sensor output occurs. The arrangement of the sensor and beams is such that complementary portions of each beam, i.e., in the embodiment shown, the lower half of upper beam 32 and the upper half of lower beam 33, fall onto the photosensor while complementary portions of each beam, i.e., the upper half of beam 32 and the lower half of beam 33, fall onto the respective covers. With circular light beams, as shown, or other beams having a light intensity distribution across the beams in the direction of the expected gradient, the complementary portions of the beams will usually be such that when added together they equal one beam. Rectangular beams having equal light intensity distribution over the beam in the direction of the expected gradient may have complementary portions which add up to less than, equal to, or greater than a single beam, as long as the complementary portions add up to the same total value throughout the entire expected range of movement of the beams to be compensated for.

Figure 10:
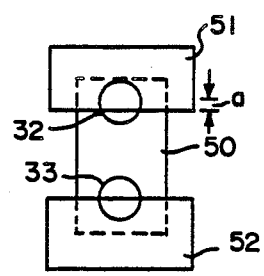

If relative movement of the probe beams take place, such as if upper beam 32 moves upwardly a distance "a", FIG. 10, due to a refractive index gradient in the sample chamber in front of beam 32, but beam 33 does not move because no refractive index gradient has yet reached a position in front of it in the sample chamber, less light from beam 32 falls on the photosensor 50 from beam 32, and only the same amount falls on photosensor 50 from beam 33 so the total light falling on photosensor 50 is reduced and its output will be reduced. It will be seen that relative movement of the two beams 32 and 33 with respect to each other, as will be caused by a refractive index gradient moving through the sample chamber, will cause either more or less light to fall onto photosensor 50 than when no relative movement takes place, and such relative movement of the two probe beams with respect to each other will cause a change in the output from the sensor. The output of the sensor will be proportional to the differences in movement between the two beams.

While the sensor of FIGS. 7–10 shows a photosensor 50 and end covers 51 and 52, the end covers merely provide sharp, defined edges for the photosensor. Thus, a photosensor without the covers could be arranged so that the light beams merely overlap the edges of the photosensor. In such instance, the positions of the two light beams may be adjusted by adjusting the distance between the Wollaston prism 28 and lens 31 so that the beams are properly positioned to fall on the edges of the photosensor. The end covers are presently preferred because it makes it easier to properly adjust the amount of each beam falling on the photosensor. Razor blades have been found to work well as end covers.

Figure 11:
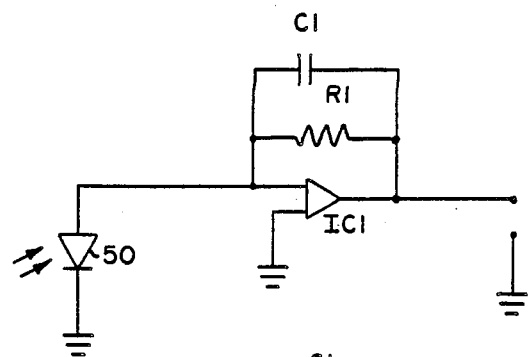

The output of the photosensor 50 provides directly the curve representative of the differences in movement between the two probe beams, i.e., the curve corresponding to curve 44 in FIG. 5. Usually the output will be amplified prior to being fed to a chart recorder, computer, or other equipment which will utilize the signal and a simple amplifier circuit as shown in FIG. 11 may be used. The photosensor 50, such as the photodiode indicated above, is connected to one input of an operational amplifier IC1 such as an OPA-111 manufactured by Burr Brown of Tuscon, Arizona. The gain of the amplifier is set in normal fashion by feedback resistor R1 and the bandwidth of the amplifier is set by capacitor C1. The circuitry is set to operate in the substantially linear range of the photodiode 50 and the light normally falling on it is not sufficient to saturate it. Thus, as the light falling on the photodiode varies, the current flowing through it, and thus the voltage across it, varies. The varying voltage is amplified by IC1 and provides the output.

Figure 12:
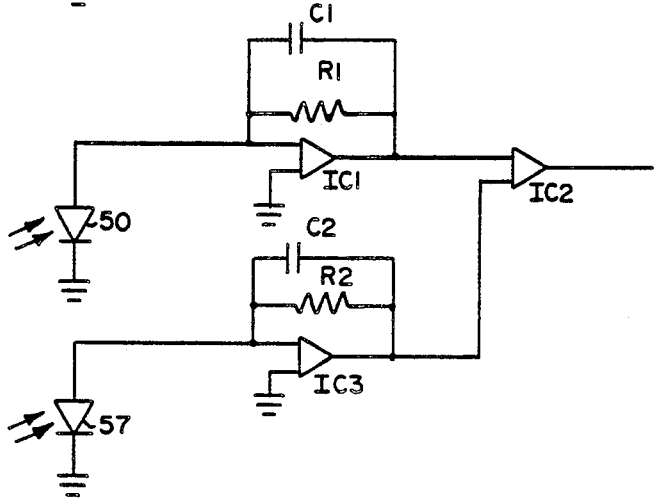

If it is desired to compensate the output of the photosensor for any intensity variations in the light beam intensity, a compensation circuit such as shown in FIG. 12, can be used. In such instance, the laser beam 26 from laser 25 may be split as by placing a glass slide 55, FIG. 13, in such beam to deflect a portion of the beam as a reference beam 56 to a photosensor 57, such as a photodiode similar to that used for sensor 50.

The circuit of FIG. 12 contains the circuitry of FIG. 11 with the output of IC1 connected to an input of differential amplifier IC2 which may be OPA101 manufactured by Burr Brown. The output of photosensor 57, which varies if the intensity of the laser beam generating the probe beam varies is amplified similarly to the output of photodiode 50 with IC3, R2 and C2 operating similarly to the amplifier previously described. The output of IC3 is connected to the other input of differential amplifier IC2 so that the output of IC2 is a signal representative of the output of photodiode 50, but compensated for any change in light intesntity of the probe beam.

Figure 13:
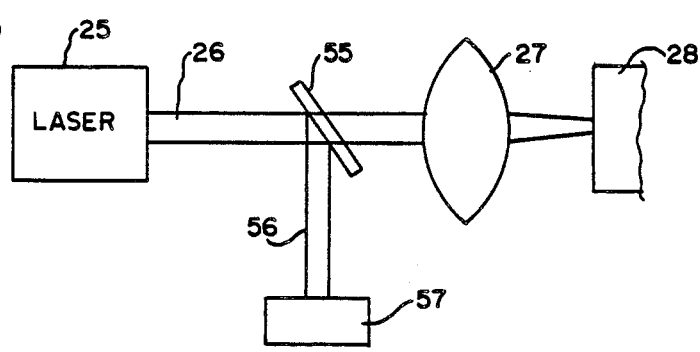
Figure 14:
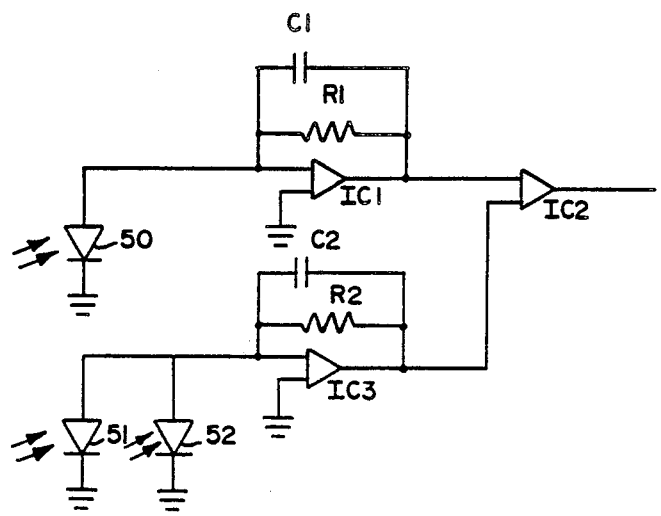

Rather than generating a separate reference beam 56 as shown in FIG. 13, the end covers 51 and 52 for photosensor 50 could themselves be additional photosensors, such as photodiodes. In such case, the photodiode end covers could be substituted directly in the circuitry of FIG. 12 for photodiode 57, as shown in FIG. 14, and serve to compensate the output of photodiode 50 for any light intensity fluctuations.

Figure 15:
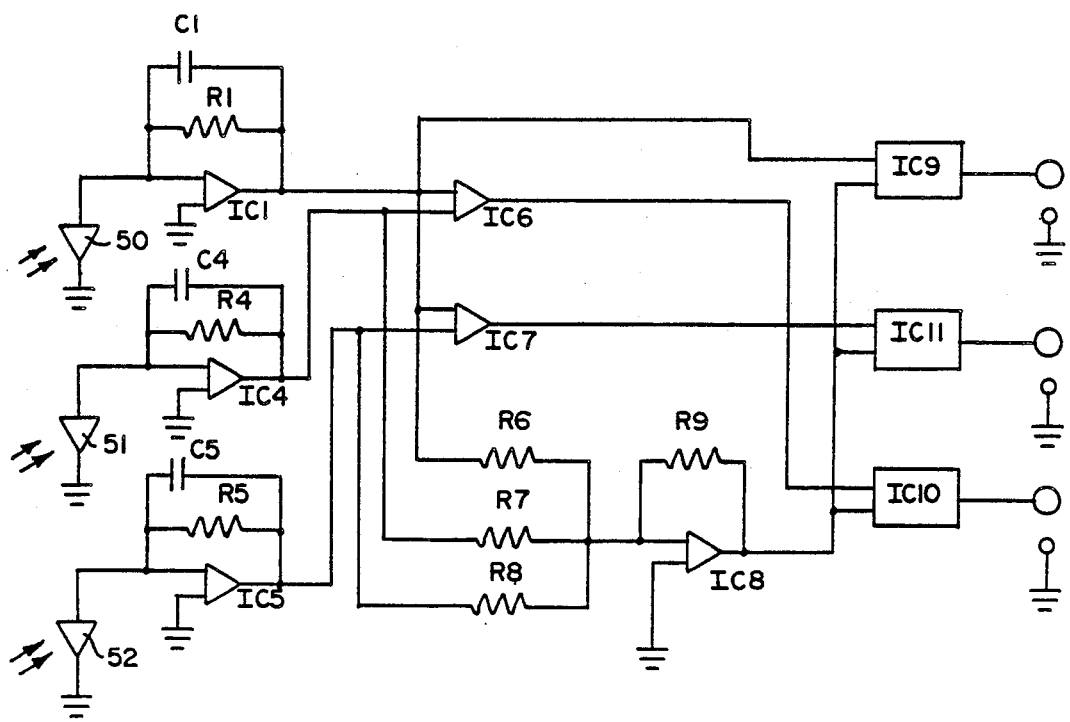

If end covers 51 and 52 are themselves photosensors, each of the covers, in combination with photosensor 50, can form an individual position detector for an individual probe beam, if desired. Circuitry showing individual beam positions as well as the difference in movement of the beams is shown in FIG. 15. Each of the three photodiodes 50, 51, and 52 have their own amplifier circuitry similar to the circuitry of FIG. 11. Thus, photodiode 50 has amplifier circuitry labeled identically to FIG. 11. The amplifier for upper photodiode 51 is made up of operational amplifier IC4, resistor R4 and capacitor C4. The amplifier for lower photodiode 52 is made up of operational amplifier IC5, resistor R5, and capacitor C5. The outputs of IC1 and IC4 are inputs to differential amplifier IC6 which measures the difference or change in light falling on photodiodes 50 and 51, respectively. The outputs of IC1 and IC5 are inputs to differential amplifier IC7 which measures the difference or change in light falling on photodiodes 50 and 52, respectively. The outputs of IC1, IC4, and IC5, which represent the total light falling on all three photodiodes, and thus the total illumination of the photodiodes provided by the probe beams, are passed through summing resistors R6, R7, and R8 to the input of operational amplifier IC8 which acts as a summing amplifier. Gain is determined by resistor R9. In order to provide the signal from photodiode 50 approximately equal to the differential of the refractive index gradients, and compensated for illumination intensity variations, the output of IC1 is connected to an input of a divider IC9 such as a DIV 100 made by Burr Brown. The output of IC8, the signal representative of total illumination intensity, is also connected as an input to IC9. The output of IC9 is the desired derivative signal compensated for intensity fluctuations. The output of IC6 is connected as an input along with the output of IC8 to divider IC10 to produce a signal proportional to the position of upper beam 32 compensated for light intensity fluctuations. Similarly, the output of IC7 is connected as an input along with the output of IC8 to divider IC11 to produce a signal proportional to the position of lower beam 33 compensated for light intensity fluctuations. These position signals may be used as desired.

Figure 16:
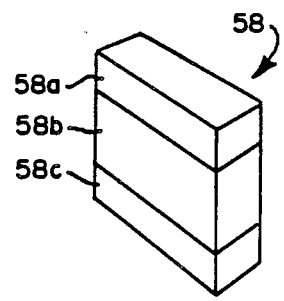

Rather than using a photodiode 50 with separate end covers 51 and 52 which are also photodiodes, a triple photodiode 58, FIG. 16, may be fabricated having individual photodiodes 58a, 58b, and 58c built together as a single unit. Such a sensor would be used as described for the sensor of FIGS. 7-10 with the photodiodes 58a, 58b, and 58c replacing photodiodes 51, 50, and 52, respectively, in the various circuits described.

Figure 17:
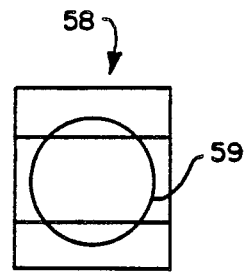

As mentioned earlier, rather than using two separate light beams, a single beam can be used. FIG. 17 shows the sensor 58 of FIG. 16 with a single beam 59 thereon. The single beam is projected through the sample chamber to fall on the sensor as shown. Parallel movement of the beam will be compensated for while movement of portions of the beam to change the intensity distribution in the beam will be detected similarly to differential or respective movement of the two beams, as described. The same detector circuitry can be used. It is presently preferred to use two beams rather than a single beam because with two beams the higher intensity centers of the beams are directed on the edges of the sensing surface of the sensors which results in increased sensitivity with the two beams as opposed to the single, larger beam.

Experimental measurement of inaccuracies due to laser positional drift indicates two orders of magnitude reduction for the differential sequential system of the invention compared to a single laser beam system, such as shown in my referenced U.S. Pat. No. 4,784,494.

Figure 18:
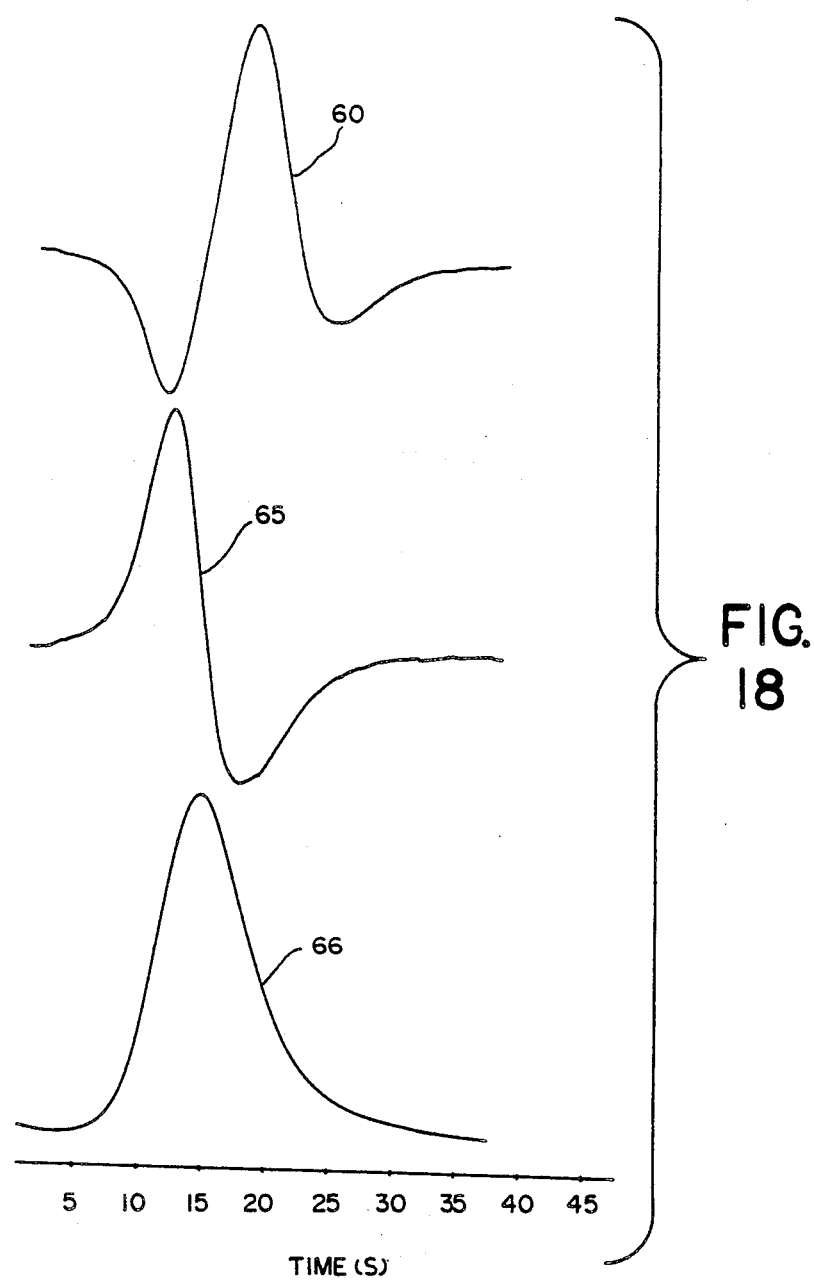

Experiments using the detector of FIG. 6 and sample flow injection to create concentration gradients in a sample chamber show that the sequential differential detector of the invention can accurately detect concentration gradients and produce a curve very close to a second derivative of the concentration gradient profile and can distinguish between high and low gradients. Typical results of such tests are shown in FIG. 18 wherein top curve 60 shows a typical signal produced by the detector of the invention in response to injecting about 4 nL of $6.4 \times 10^{-5}$M of sucrose into a sample chamber, shown schematically in FIG. 19. The sample chamber was a 200 $\mu$m inside diameter square tube 61 with a 25 $\mu$m inside diameter open tubular capillary column 62 inserted into one end. The end of the capillary inside the square tube 61 which delivered the sample was carefully sharpened. Pure solvent was supplied around the capillary, as at arrows 63, to produce a sheath flow to provide the solvent into which the sucrose, arrow 64, was injected. The solvent and sample flows were generated with the help of two syringe pumps, not shown, (Model 249-2, Sage Instruments, Inc., White Plains, NY). The sample was injected by use of a switching valve, not shown, equipped with a high-speed switching accessory kit and digital value interface (Valco Instruments Co., Inc., Houston, TX). This allowed the operation of the experiment by a Leading Edge IBM compatible microcomputer, also not shown. The front of the injection produces a substantially higher differential concentration gradient signal than the tail. The second curve, labeled 65 in FIG. 18, shows the refractive index gradient signal reconstructed from the detector response curve 60. The third curve, labeled 66 in FIG. 18, is attained by integrating curve 63 and represents the sucrose concentration profile in the solvent. The dramatic difference between the front and tail, shown in curve 60, is not as easily noticeable in reconstructed and integrated curve 66. This comparison indicates the increased ability to distinguish between high and low gradients by generating a signal directly which approximates a derivative. Also, the second derivative signal, curve 60, is much sharper than the Gaussian concentration peak shown by curve 66. This can enable an increase of the throughput of flow injection analysis.

The maximum sensitivity in the detection system is achieved when the distance between the two probe beams is close to $2\sigma$ of the sample peaks generated during an experiment. In this case, one beam is experiencing the highest negative concentration gradient while the other one the highest positive. Therefore, the maximum change in light flux irradiating the photosensor is produced which results in high signal amplitude. In the flow injection experiment described here, this distance corresponds to about 200 $\mu$m. The concentration detection limit of this detector was close to $7 \times 10^{-7}$M of sucrose solution (signal to noise ratio of about 3:1). This is an improvement of close to an order of magnitude compared to a single beam experiment as with the system of my referenced patent.

The width of the individual probe beams used with the detector of the invention should be small with respect to the peak being measured and preferably should be no more than about ½σ of the peak being measured or about one tenth of the width of the peak. If larger in width, many of the advantages of the dual beam system are lost.

Figure 20:
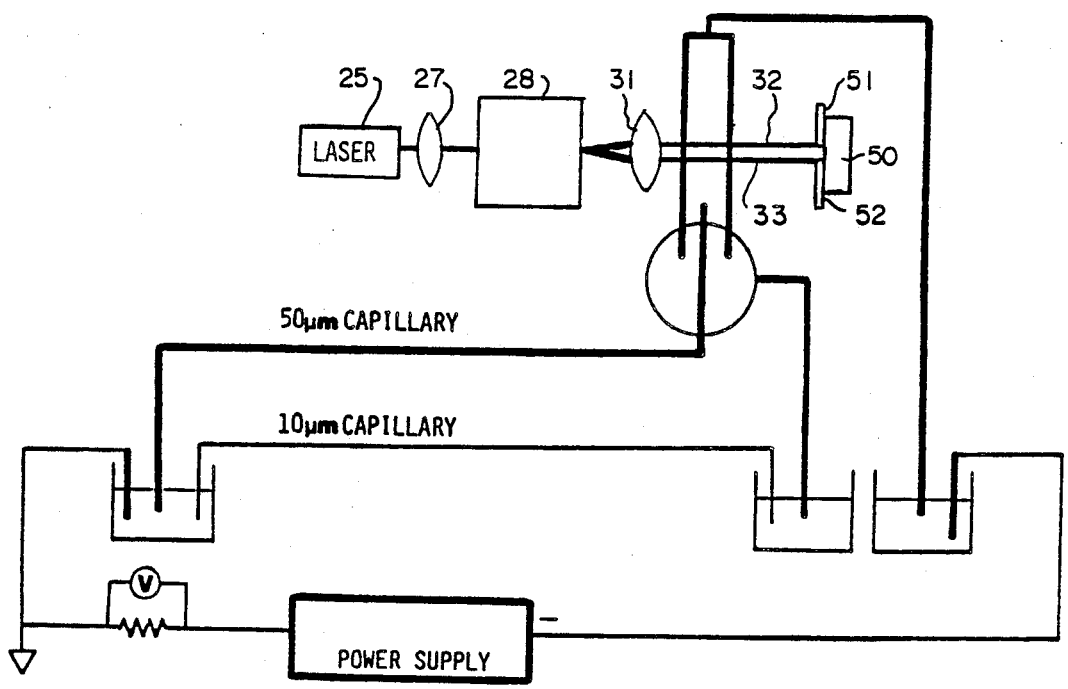
Figure 19:
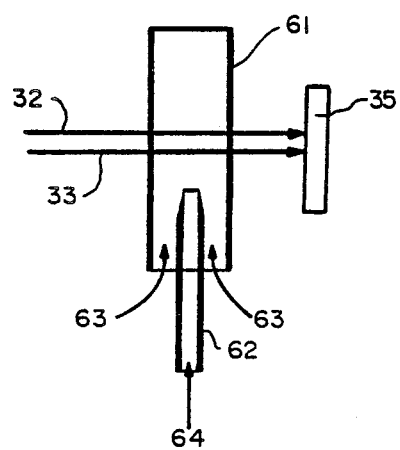

The detector of the invention was also tested in capillary zone electrophoresis experiments. The electrophoretic apparatus is shown in FIG. 20. The separation in the apparatus occurs in 50 cm of the 50 μm fused silica capillary (Spectran Corp., Sturgridge, MA). A high voltage power supply (Spellman, Plainview, NY) was used to provide a 10,000 V potential for the electrophoresis separations. Electrodes were made with platinum wire. The detector cell was identical to that used in flow injection analysis as shown in FIG. 19. The sheath flow was generated electrokinetically and regulated by using an appropriate length of 10 μm fused silica tubing which worked as a voltage drop resistor. The injection was produced electrokinetically by applying 10 kV voltage to a sample solution for a few seconds. The separation was performed in a phosphate buffer at pH7. The sample mixture and buffer was degassed by filtering through 0.2 μm pore size cellulose nitrate membranes (Watman Limited, Maidstone, England).

FIG. 21 shows the electrophorogram of three amino acids obtained with the apparatus of FIG. 16. All peaks appear to be well separated, but in fact, they are not fully resolved. This is indicated by FIG. 22, which shows an electrophorogram corresponding to the concentration profile of the amino acids. The second order derivative, FIG. 21, as produced by the detector of the invention, produces a peak with a width close to 4σ while the Gaussian width of the concentration distribution is close to 6σ. It is also possible to notice large drifts of the baseline of FIG. 22. The reconstruction and integration of the curve of FIG. 21 to obtain the curve of FIG. 22 converted the vertical axis of FIG. 21 from the differential refractive index gradient into the refractive index. Now the drifts, due to temperature variation, are easily noticed. This shows that the drift is dramatically reduced in the differential gradient signal due to the filtering properties of the detector of the invention.

The detector of the invention is useful anytime differences between movement of probe beams is important and can be used in various measurements, such as refractive index measurements, as well as the applications described here in detail. In addition, it can be used for frontal analysis in physico-chemical studies. Introduction of a well defined "slope injection" will not only generate the chromatogram, but also detect any changes in dynamics of separation. This approach can replace a multiple frontal analysis approach.

The invention also includes the method of detecting the refractive index gradients by using two probe beams and a detector that directly produces an output signal indicative of the difference in movement of the two probe beams.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A detector for detecting refractive index gradients within a sample, comprising means for generating two closely spaced, parallel probe light beams; means for passing the light beams through the sample so that the light beams are separated along the direction of the expected refractive index gradient; a sensor located in the path of both of the beams after passing through the sample and adapted to measure only complementary portions of each beam when no refractive index gradient is present in the sample so that parallel movement of the beams will change equally the respective complementary portions sensed to maintain a constant output from the sensor, but movement of one beam relative to the other will produce an output proportional to the relative movement.

2. A detector according to claim 1, wherein the refractive index gradient to be measured is caused by a concentration gradient of a component within the sample and the output of the sensor is a signal approximating the second derivative of the concentration of the component causing the concentration gradient.

3. A detector according to claim 1, wherein the sensor is a photosensor having a sensing surface, and wherein the photosensor is arranged with respect to each of the probe beams so that only the complementary portions of each beam to be measured fall onto the sensing surface of the photosensor.

4. A detector according to claim 3, wherein the sensing surface of the photosensor is defined by a mask covering a portion of the sensing surface to prevent any portion of a beam falling on the mask from falling on the sensing surface of the photosensor.

5. A detector according to claim 4, wherein a mask is located along each of two opposite sides of the photosensor to provide two opposite sharply defined edges of the sensing surface along said two opposite sides, wherein the opposited edges are transverse to the direction of expected refractive index gradients to be detected, and wherein respective probe beams and the photosensor are arranged so that each probe beam falls partially on the sensing surface of the photosensor and partially on a mask.

6. A detector according to claim 5, wherein the respective probe beams and the photosensor are arranged so that with no refractive index gradient in the path of the respective probe beams, the sum of the complementary portions of the respective probe beams falling on the sensing surface of the photosensor will remain the same through an expected range of parallel movements of the probe beams with respect to the photosensor.

7. A detector according to claim 5, wherein the masks are also photosensors which sense the portions of the probe beams falling on the masks.

8. A detector according to claim 6, wherein the sum of the complementary portions of the respective probe beams falling on the sensing surface of the photosensor when no refractive index gradient is in the path of the respective beams is equal to a single one of the probe beams falling completely on the sensing surface of the photosensor.

9. A detector according to claim 8, wherein the sensing surface of the photosensor may be variably defined so as to adjust the sensing surface so that only the complementary portions of each beam to be measured fall onto the sensing surface of the photosensor.

10. A detector according to claim 8, wherein the photosensor is a photodiode.

11. A detector according to claim 1, wherein the probe light beams are generated by a laser.

12. A detector according to claim 11, wherein the two probe light beams are generated from a single laser beam by splitting the single laser beam into the two beams.

13. A detector according to claim 1, wherein the refractive index gradient to be measured is caused by a concentration gradient of a component within the sample, wherein the concentration of the component in the sample causing the concentration gradient has a Gaussian profile, and wherein the distance between the probe beams is approximately equal to $2\sigma$ of the expected Guassian profile causing the refractive index gradient to be measured.

14. A detector according to claim 13, wherein the width of each of the probe beams is less than about $\frac{1}{2}\sigma$.

15. A method of detecting refractive index gradients within a sample, and producing an output signal approximately representative of a derivative of the refractive index gradient, comprising the steps of passing two closely spaced, parallel light beams through a sample which may contain the refractive index gradient to be detected, the two beams being separated along the direction of the expected refractive index gradient; providing a photosensor having a sensing area and well defined edges of the sensing area; positioning the photosensor so that the well defined edges are transverse to the direction of the expected refractive index gradient; aligning the photosensor and the light beams so that with no refractive index present in the sample through which the light beams pass, only complimentary portions of each light beam will fall onto the sensing area of the photosensor whereby parallel movement of the beams will change equally the respective complimentary portions sensed to maintain a constant output for the sensor, but movement of one beam relative to the other will produce a change in the output of the sensor proportional to the relative movement.

16. A method of detecting refractive index gradients according to claim 15, wherein the step of providing a photosensor having a sensing area and well defined edges includes the steps of providing a photosensor and masks in connection with the photosensor and over a portion of the sensing area thereof to provide the well defined edges of the sensing area.

17. A detector for detecting refractive index gradients within a sample along a gradient direction and providing an output approximating a derivative of the refractive index gradient detected, comprising a sensor having a sensing surface extending along the direction of the expected gradient to be detected for a distance less than the length of the expected gradient; a source of light; means for directing the light through the sample so that a portion of the light falls on the sensing surface of the sensor, a portion of the light falls off the sensing surface of the sensor on one side of the sensing surface along the gradient direction, and a poriton of the light falls off the sensing surface of the sensor on the opposite side of the sensing surface along the gradient direction, and wherein the portions of the light falling off the sensing surface of the sensor on opposite sides thereof are complementary portions so that movement of the light not caused by presence of a refractive index gradient in the path of the light will move equally, in the same direction, the respective complementary portions of the light so that the same amount of light falls on the surface of the sensor to maintain a constant output from the sensor, but movement of the complementing portions with respect to one another as caused by a refractive index gradient in the path of the light will produce an output proportional to the relative movement.

18. A detector according to claim 17, wherein the light passing through the sample is in the form of a single light beam.

19. A detector according to claim 17, wherein the light passing through the sample is in the form of a pair of spaced light beams.

* * * * *